US008029506B2

(12) United States Patent
Levy et al.

(10) Patent No.: US 8,029,506 B2
(45) Date of Patent: Oct. 4, 2011

(54) BONE FRACTURE TREATMENT DEVICES AND METHODS OF THEIR USE

(75) Inventors: Mark M. Levy, Raanana (IL); Ilan Greenberg, Haifa (IL)

(73) Assignee: Expanding Orthopedics Inc., Memphis, TN (US)

( * ) Notice: Subject to any disclaimer, the term of this patent is extended or adjusted under 35 U.S.C. 154(b) by 0 days.

(21) Appl. No.: 12/859,001

(22) Filed: Aug. 18, 2010

(65) Prior Publication Data
US 2010/0331841 A1 Dec. 30, 2010

Related U.S. Application Data

(63) Continuation of application No. 11/036,304, filed on Jan. 13, 2005, now Pat. No. 7,828,802.

(60) Provisional application No. 60/536,918, filed on Jan. 16, 2004.

(51) Int. Cl.
*A61B 17/72* (2006.01)

(52) U.S. Cl. ........................................ 606/63

(58) Field of Classification Search .............. 606/62–68, 606/74, 300–304, 309, 310, 313, 325–327; 411/21, 46, 48, 59–61, 69
See application file for complete search history.

(56) References Cited

U.S. PATENT DOCUMENTS

| 5,437,674 | A | * | 8/1995 | Worcel et al. | 606/308 |
| 6,179,873 | B1 | * | 1/2001 | Zientek | 623/17.11 |
| 6,319,255 | B1 | * | 11/2001 | Grundei et al. | 606/76 |
| 6,447,513 | B1 | * | 9/2002 | Griggs | 606/62 |
| 7,828,802 | B2 | * | 11/2010 | Levy et al. | 606/63 |

* cited by examiner

*Primary Examiner* — Eduardo C Robert
*Assistant Examiner* — Steven Cotroneo
(74) *Attorney, Agent, or Firm* — Dekel Patent Ltd.; David Klein

(57) ABSTRACT

A bone treatment device comprises a shaft having a tubular wall, a lumen extending within the tubular wall, openings through the tubular wall, and anchoring elements adjacent the openings that can be deployed out of the openings in the presence of an actuating force within the shaft lumen. The bone treatment device may further comprise an actuator configured to be received within the shaft lumen to deploy the anchoring elements out of the openings.

26 Claims, 12 Drawing Sheets

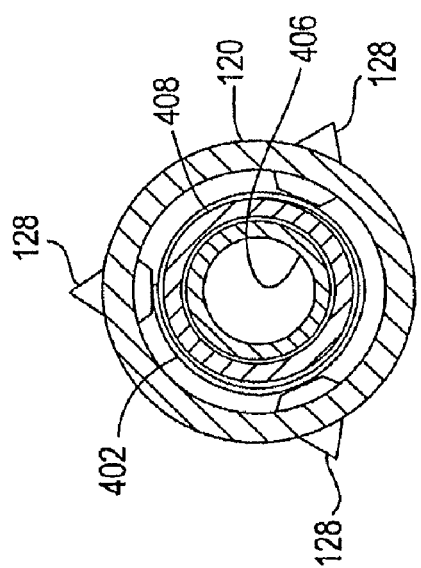

BONE FRACTURE TREATMENT DEVICES AND METHODS OF THEIR USE

CROSS REFERENCE TO RELATED APPLICATIONS

This application is a continuation application that claims the benefit of co-pending U.S. patent application Ser. No. 11/036,304, filed Jan. 13, 2005, which is herein incorporated by reference in its entirety. The present application also claims priority under 35 U.S.C. §119 to U.S. Provisional Patent Application Ser. No. 60/536,918, entitled "Intramedullary Devices and Methods of Using Same" filed Jan. 16, 2004, the complete contents of which are incorporated herein by reference.

FIELD OF THE INVENTION

This invention relates generally to medical devices and methods and, more specifically, to devices and methods for stabilizing fractured bones and/or for fixing objects to bones.

BACKGROUND OF THE INVENTION

Fractures of limb bones have been treated with internal fixation devices, such as plates lying on the surface of a bone, nails running inside the medullary canal of a fractured bone, and/or screws affixing both ends of a fractured bone together. These internal fixation devices may provide reasonable structural rigidity and/or stability to the fractured bone without compromising some of the strain desired to stimulate bone cells.

An intramedullary fixation method is a traditional procedure for treating long bone fractures, which involves affixing the bone fracture using intramedullary nails, without disturbing the periosteum of the bone. Such a method may be accomplished in a closed manner, and the fractured bone may be functionally used (including weight bearing) during healing. The surgical approach for insertion of intramedullary nails varies slightly for each bone and is well known in the field of orthopedics.

Some of the problems associated with conventional intramedullary fixation methods include lack of rotation stability (i.e., fractured bone segments connected by a nail can rotate relative to each other), lack of longitudinal stability (i.e., fractured bone segments connected by a nail can move relative to each other along an axis of the nail), collapse of the fracture site in some fracture types, and/or undesired backup of nails. In addition, intramedullary fixation methods may introduce interlocking screws across the nail, creating some disadvantages. Specifically, conventional intramedullary fixation nails for long bones may include a rigid structure (hollow or full) that may be locked at their extremes by the addition of screws transversally applied through the bone walls and the nail itself. This additional step generally makes the operation longer and more complicated, and may require additional skin incisions and/or longer use of an image intensifier (X-ray). Furthermore, undesired gaps between the bone ends may originate from the screws, which are permanent unless removed in a new operation. In contaminated fractures, metallic intramedullary nails may propagate contamination through the entire canal, despite attempts at cleaning the fracture site, which may lead to bone infection.

SUMMARY OF THE INVENTION

In accordance with a first aspect of the present inventions, a bone treatment shaft comprises a tubular wall and a lumen extending within the tubular wall. In one embodiment, the tubular wall is configured to extend within the medullary canal of the treated bone, but may alternatively be sized to laterally extend into the treated bone in its cancellous or cortical areas, or both, in long, flat or irregular bones. Embodiments of the invention are intended to be implanted using minimally invasive surgical methods, but may also be implanted in traditional open surgery.

In embodiments of the invention, the tubular wall may be cylindrical, e.g., to conform more closely to the medullary canal of the bone, or may be non-cylindrical, e.g., elliptical, triangular, rectangular, conical or tapered, with an open, partially open, or closed cross section profile. The tubular wall may also be slotted, with grooves on the surface, or threaded, to facilitate anchoring of the shaft within the bone. The tubular wall may have a substantially continuous surface, e.g., to inhibit bone growth onto the shaft, thereby facilitating subsequent removal of the shaft from the bone. Alternatively, the tubular wall may be porous, e.g., composed of a mesh, in order to promote bone growth within the tubular wall, thereby facilitating anchoring of the shaft, or even coated (in the continuous or mesh type) with bone inducer factors for better bone adherence. Such coatings may include antibiotics, immobilized enzymes, other drugs, polymers, ceramics, or any other biocompatible substance.

The shaft further comprises at least one opening through the tubular wall, and at least one bone anchoring element adjacent the opening(s) that is configured to be deployed out of the opening(s) in the presence of an actuating force within the lumen. In one embodiment, the anchoring element(s) is hingedly coupled to the tubular wall, and may be formed with the tubular wall as a unibody structure. In such cases, the opening is similar or slightly bigger than the anchoring element. If hingedly coupled, the anchoring element(s) can be deployed by hinging the anchoring element(s) outward away from the lumen. In other embodiments, the anchoring element(s) may be welded to the shaft, in which cases, the opening(s) may or may not be similar to the anchoring element(s). In another embodiment, the anchoring elements are deployed inward, when the tubular wall, or sections of it, is placed on the surface of the bone.

The anchoring element(s) may optionally comprise an outwardly extending sharp tip. In this manner, the anchoring element(s) can more effectively anchor the shaft within the bone. In one embodiment, the anchoring element(s) is plastically deformable, so that it remains deployed even if the actuating force is removed from the lumen. Alternatively, however, the anchoring element(s) can be elastically deformable, in which case, the anchoring element(s) may remain deployed by its adhesion to the bone and/or the maintenance of the actuating force. Also, in some embodiments, the anchoring element(s) can be deformed in part elastically and in part plastically. If a plurality of openings, and thus anchoring elements, are provided, they can axially extend along the tubular wall to provide an anchoring force along the shaft and/or they may extend around the tubular wall to provide an anchoring force around the shaft. The openings and anchoring elements may be disposed on the tubular wall in patterned sets or in a random configuration, along the entire length of the shaft, or at portion(s) of the shaft, such as, at one or both ends of the shaft. The anchoring elements can have the same or different shapes and/or sizes.

In accordance with a second aspect of the present inventions, a bone treatment kit comprises the bone treatment shaft and an actuator is provided. The actuator is configured to be received within the shaft lumen to deploy the anchoring element(s) out of the opening(s). The actuator may be variously configured. For example, the actuator may comprise a member configured to slide within the shaft lumen to deploy the anchoring element(s) out of the opening(s). The member may, e.g., be an elongated member or a pellet-shaped member. In the latter case, multiple pellet-shaped member can be introduced within the shaft lumen to deploy multiple anchoring element(s). The member may be configured to selectively deploy anchor element(s).

For example, the member may be placed within a first rotational orientation that does not deploy a selected anchoring element when the member is slid by the anchoring element, and in a second rotational orientation that deploys the selected anchoring element when the member is slid by the anchoring element. The actuator may optionally comprise an expandable member configured to expand within the shaft lumen to deploy the anchoring element(s) out of the opening (s). For example, the expandable member may be a spiraled tube disposed within the shaft lumen that expands within the shaft lumen when the member slides through the spiraled tube. Another member can be slid over the first member to further expand the spiraled tube. The expandable member may alternatively be a balloon or balloon actuating device.

In accordance with a third aspect of the present inventions, a method for treating the bone is provided. The method comprises inserting the bone treatment device into the bone, e.g., along the medullary canal of the bone or laterally into the bone. The method further comprises deploying the anchoring element(s) out of the opening(s) (e.g., by using one of the previously described actuators) to anchor the device within the bone, e.g., by hinging the anchoring element(s) outward from the tubular wall. If the bone is fractured, anchoring of the device will help stabilize the fractured bone.

In embodiments in which the tubular wall, or sections of it, is placed on the surface of the bone and the anchoring elements are pointing inwards, the actuator will comprise a similar geometric form, but will be slightly oversized to deploy the anchors through the openings to engage the bone wall.

Other aspects and features of the invention will be evident from reading the following detailed description of the illustrated embodiments, which are intended as examples, and not to limit, the invention.

BRIEF DESCRIPTION OF THE DRAWINGS

The drawings illustrate the design and utility of embodiments of the present invention, in which:

FIGS. 6A-6C are cross-sectional views of the bone treatment kit of FIG. 5 at different stages during use;

DETAILED DESCRIPTION OF THE ILLUSTRATED EMBODIMENTS

Figure 1:
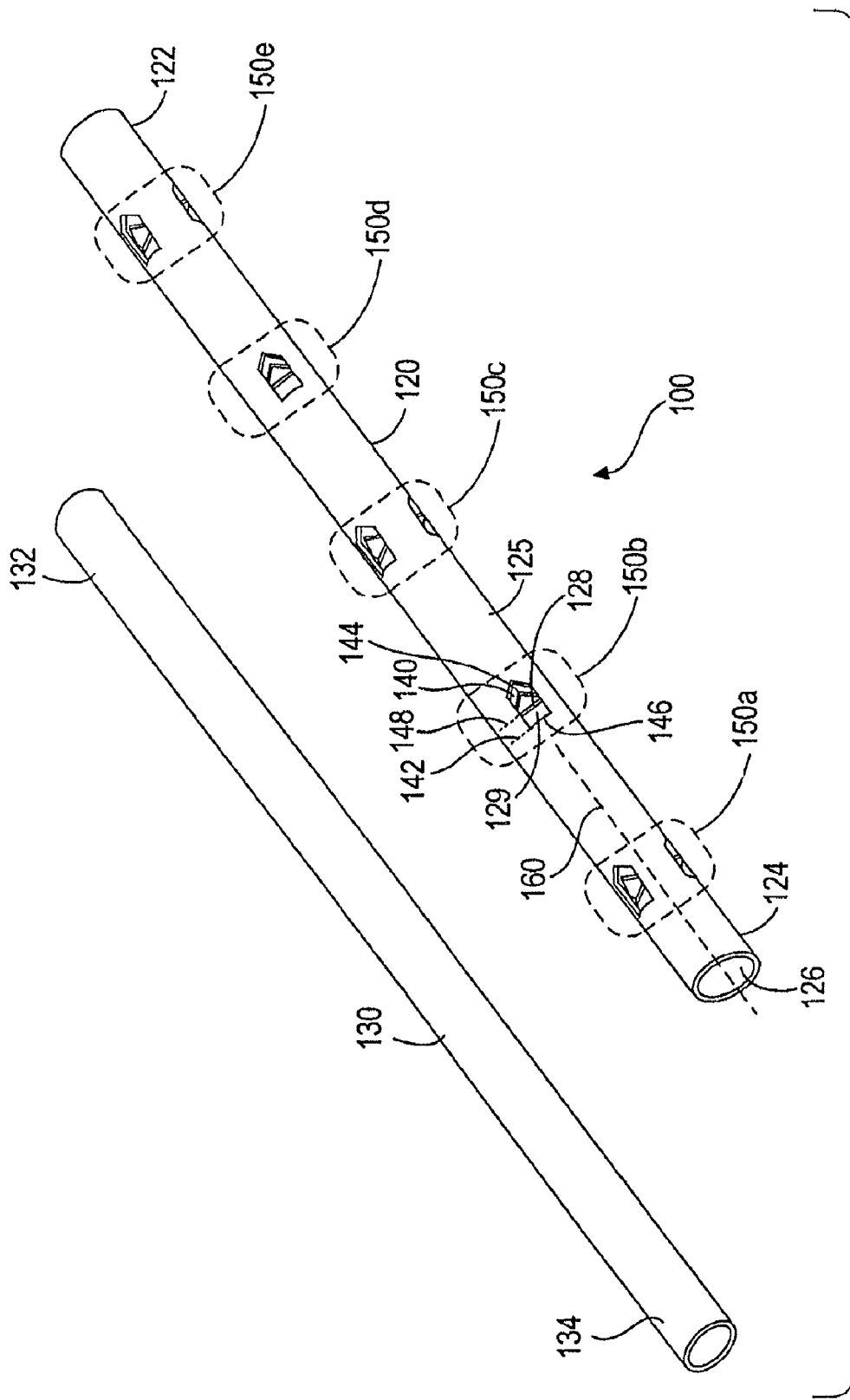
FIG. 1 is a perspective view a bone treatment kit constructed in accordance with one embodiment of the invention, particularly showing a cylindrical intramedullary bone shaft and an actuator.
Figure 2:
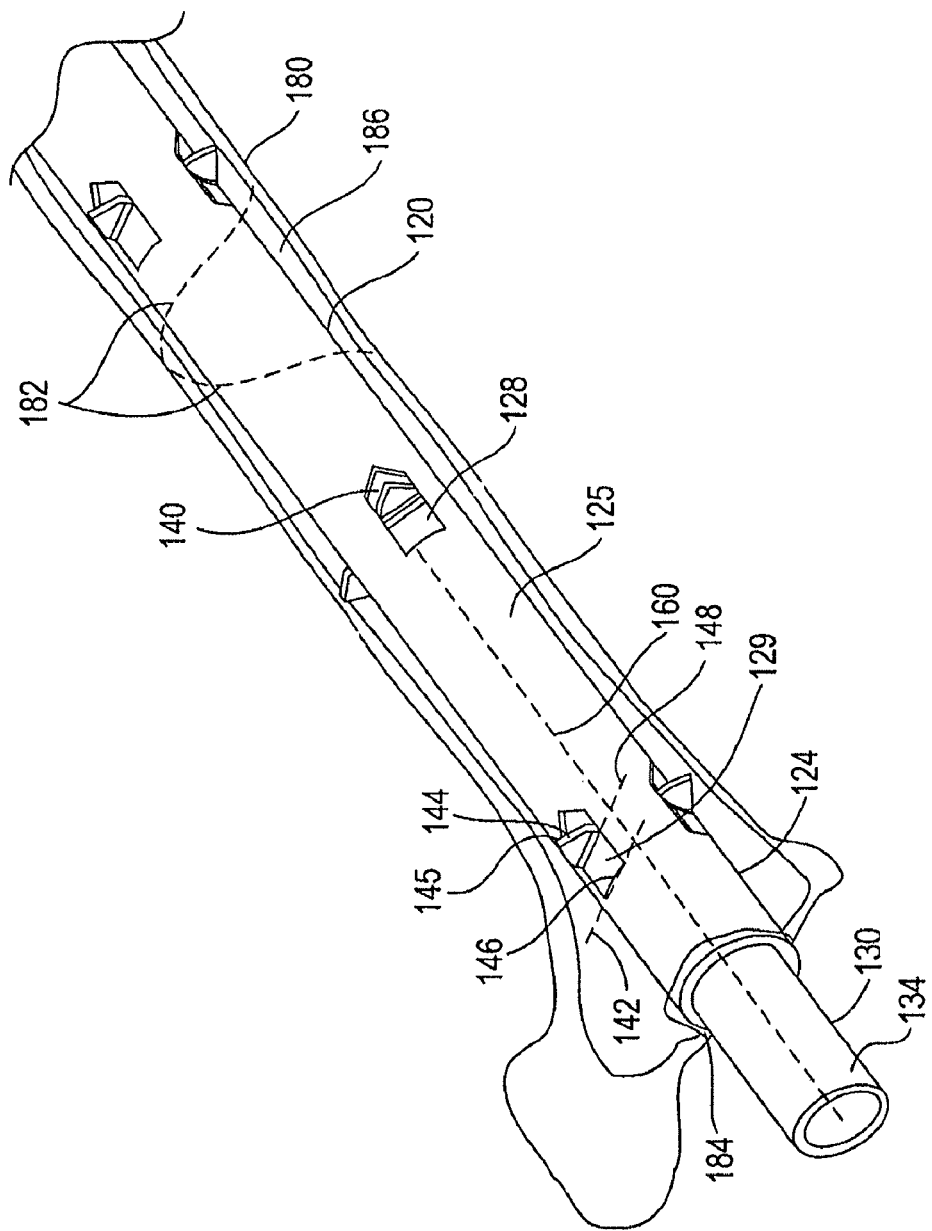
FIG. 2 is a perspective view of the intramedullary bone shaft anchored within the medullary canal of a bone using the actuator of FIG. 1.

Referring now to FIGS. 1 and 2, a bone treatment kit 100 in accordance with one embodiment of the invention will now be described. The kit 100 generally comprises a bone treatment shaft 120 and an actuator 130 that facilitates anchoring of the bone treatment shaft 120 along a medullary canal of a bone. The bone shaft 120 has a first end 122, a second end 124, and a tubular wall 125 defining a lumen 126 that extends between the first and the second ends 122, 124. The actuator 130 has a first end 132 and a second end 134. The actuator 130 is sized such that it can be inserted into the lumen 126 of the bone shaft 120 during use. The bone shaft 120 and the actuator 130 can be made from a variety of biocompatible materials, such as plastics, polymer, metals, alloys, or ceramics. The bone shaft 120 and the actuator 130 can also be made from a bioabsorbable material, a tissue engineered material, a shape memory alloy or polymer, such as, nitinol, or other resilient materials, such as stainless steel or a titanium alloy, or combinations of both bioabsorbable, or tissue engineered, and non-bioabsorbable materials. Preferably, the bone shaft 120 is rigid enough to provide stability to the fractured bone in which it will be anchored, or to provide structural rigidity to properly fix other structures to the bone.

The bone shaft 120 includes a plurality of anchoring elements 128 hingedly coupled to the tubular wall 125 and a plurality of respective openings 140 formed through the tubular wall 125. Each anchoring element 128 has a first end 144 having a sharp tip 145, and a second end 146 that is secured to the wall 125 of the bone shaft 120 (FIG. 2). In alternative embodiments, instead of a single sharp tip 145, the anchoring element 128 can have a plurality of sharp tips. In other embodiments, the anchoring element 128 can have side sections that are sharp. Also in further embodiments, the anchoring element 128 can have an end that is not sharp (e.g., a blunt tip). In the illustrated embodiment, the anchoring elements 128 and tubular wall 125 are formed as a unibody structure. For example, each anchoring element 128 and each respective opening 140 are made by cutting through the wall 125 of the bone shaft 120, such that a portion 129 (defined by a profile of the cut) of the wall 125 can be bent. The cutting can be accomplished using a laser beam or a mechanical cutter. The first end 144 of the portion 129 is then bent along a first line 148 and away from the axis 160 to create a spike or thorn that points radially away from the axis 160. The portion 129 is then bent along a second line 142 to place the portion 129 into the lumen 126. It should be noted that instead of the cut profile shown, in alternative embodiments, different cut profiles can be used to create different shapes for the openings 140 and the anchoring elements 128. In addition, instead of making the anchoring element 128 from a portion of the wall 125, the anchoring element 128 can be separately manufactured and then secured to the bone shaft 120 using a glue, a weld, or a suitable adhesive.

In the illustrated embodiment, the bone shaft 120 includes five sets 150a-e of the anchoring elements 128 disposed along the axis 160 of the bone shaft 120, with each of the sets 150a-e having three anchoring elements 128 circumferentially disposed about the axis 160 of the bone shaft 120. In alternative embodiments, instead of having five sets of three anchoring elements 128, the bone shaft 120 can include other number of sets, and each of the sets can include other number of anchoring elements 128. In the illustrated embodiment, the anchoring elements 128 in one of the sets 150 can be circumferentially aligned with the anchoring elements in an adjacent set 150. Alternatively, the anchoring elements 128 of adjacent sets 150 may not be circumferentially aligned. Furthermore, in alternative embodiments, instead of having a regular or a well-defined pattern, the anchoring elements 128 can be randomly disposed along the length of the bone shaft 120. In any of the embodiments described herein, the anchoring elements 128 can have the same or different shapes and/or sizes.

In the illustrated embodiment, the actuator 130 is an elongated member that has a cross-sectional dimension that is smaller than a cross-sectional dimension of the lumen 126, thereby allowing the actuator 130 to be inserted into the lumen 126. The cross-sectional dimension of the actuator 130 should also be large enough such that when the actuator 130 is placed within the lumen 126, an exterior surface of the actuator 130 can engage all of the anchoring elements 128 to deploy the anchoring elements 128 (FIG. 2). In one embodiment, the cross-sectional dimension of the actuator 130 is slightly (e.g., ⅛") smaller than the cross-sectional dimension of the lumen 126, thereby allowing the actuator 130 to deploy the anchoring elements 128 out of the lumen 126 through the respective openings 140. In another embodiment, the cross-sectional dimension of the actuator 130 can be made smaller to control a degree of deployment of the anchoring elements 128. In the illustrated embodiment, the anchoring elements 128 undergo plastic deformation as they are deployed. Alternatively, the bone shaft 120 can be constructed from a relatively more elastic material, which allows the anchoring elements 128 to undergo elastic deformation as they are being deployed. Also, in other embodiments, the anchoring elements 128 can be configured to undergo deformation that is in part elastic and in part plastic. In other embodiments, shape memory materials can be used, thereby allowing the anchoring elements be deployed without the use of an actuator. In still other embodiments, the actuator can be made out of bone graft tissue, natural or synthetic bioabsorbable material, or tissue engineering material, as a scaffold for cell seeding or simply for the conduction or the induction of natural bone tissue. In some cases, a rigid actuator can be replaced by an element made out of one of the previously mentioned materials for more biological integration while supporting the anchoring elements and also both, the wall and the actuator can be made of the same type material for full integration.

As shown in FIG. 2, the bone treatment kit 100 can be used to stabilize a femur 180 having a compound fracture 182. Alternatively, the kit 100 can be used in bones other than the femur 180, such as a tibia, a humerus, a vertebra through a pedicle, or any other bone, to treat other conditions. The bone shaft 120 can inserted through a previously formed entry portal 184 into a medullary canal 186 of the femur 180 using conventional methods. Once the bone shaft 120 is desirably placed, the actuator 130 can then inserted into the lumen 126 of the bone shaft 120 at the second end 124, and advanced distally to deploy (and in the illustrated embodiment, hinging) the anchoring elements 128 out of the lumen 126 through the respective openings 140. The anchoring elements 128 penetrate into bone tissue surrounding the bone shaft 120, anchoring the bone shaft 120 to the femur 180. The anchoring elements 128 help prevent the bone shaft 120 from sliding longitudinally and/or rotating about the longitudinal axis 160 relative to the femur 180.

As will be described in further detail below, bone shaft incorporating certain anchoring features of the bone shaft 120 can be used to laterally anchor bone stabilizing structures onto the exterior of fractured bones, or to fix other devices or objects (e.g., section(s) of a joint prosthesis for arthroplasty, allograft or tissue engineered sections of joints or bones, a tendon, a ligament, a muscle, a transducer, a hook, an adaptor, a plate, a prosthetic tooth or a bridge on the jaw's bones, a tissue engineered tissue, matrix or scaffold, etc.) to any location on bones, or joints, for other applications.

Figure 3:
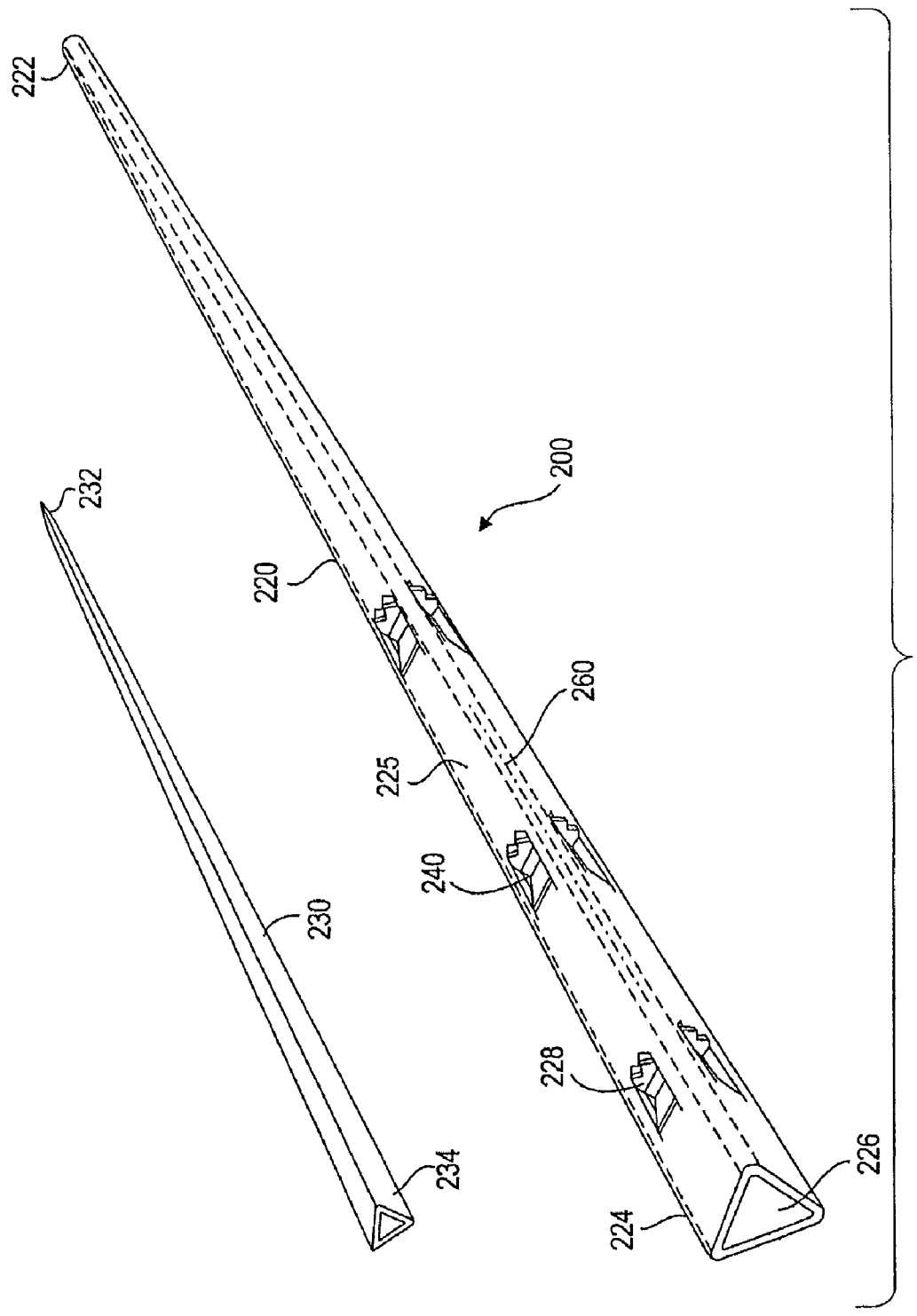
FIG. 3 is a perspective view of a bone treatment kit constructed in accordance with another embodiment of the invention, particularly showing a non-cylindrical intramedullary bone shaft and an actuator.

In the previously described embodiment, the bone shaft 120 and the actuator 130 each has a circular cross-section. Other cross-sectional shapes, however, can be provided. For example, FIG. 3 illustrates a bone treatment kit 200 that is similar to the previously described kit 100, with the exception that it comprises a tubular bone shaft 220 and actuator 230 with triangular cross-sectional shapes. The bone shaft 220 having a first end 222, a second end 224, and a wall 225 defining a lumen 226 that extends at least partially between the first and the second ends 222, 224. The bone shaft 220 also has a plurality of openings 240 and a plurality of respective anchoring elements 228 associated with the openings 240. In the illustrated embodiments, a row of three anchoring elements 228 are disposed on each side of the tubular bone shaft 220. In other embodiments, the three anchoring elements 228 on each side of the tubular bone shaft 220 may be arranged in other patterns, and the sides may have different number of anchoring elements 228. The actuator 230 has a first end 232 and a second end 234. In alternative embodiments, either or both of the bone shaft 220 and the actuator 230 can have other cross-sectional shapes, such as an elliptical, semi-circular, rectangular, or other customized shapes.

An advantage of using a non-circular shape as the cross-section of the bone shaft 220 is that the bone shaft 220, once implanted into a bone, cannot be rotated torsionally, i.e., about a longitudinal axis 260 of the bone shaft 220, thereby anchoring itself torsionally to the bone. In such case, the anchoring elements 228 serve the purposes of anchoring the bone shaft 220 to the bone such that the bone shaft 220 cannot move longitudinally within the bone, and enhancing torsional anchorage of the bone shaft 220 to the bone.

Figure 4:
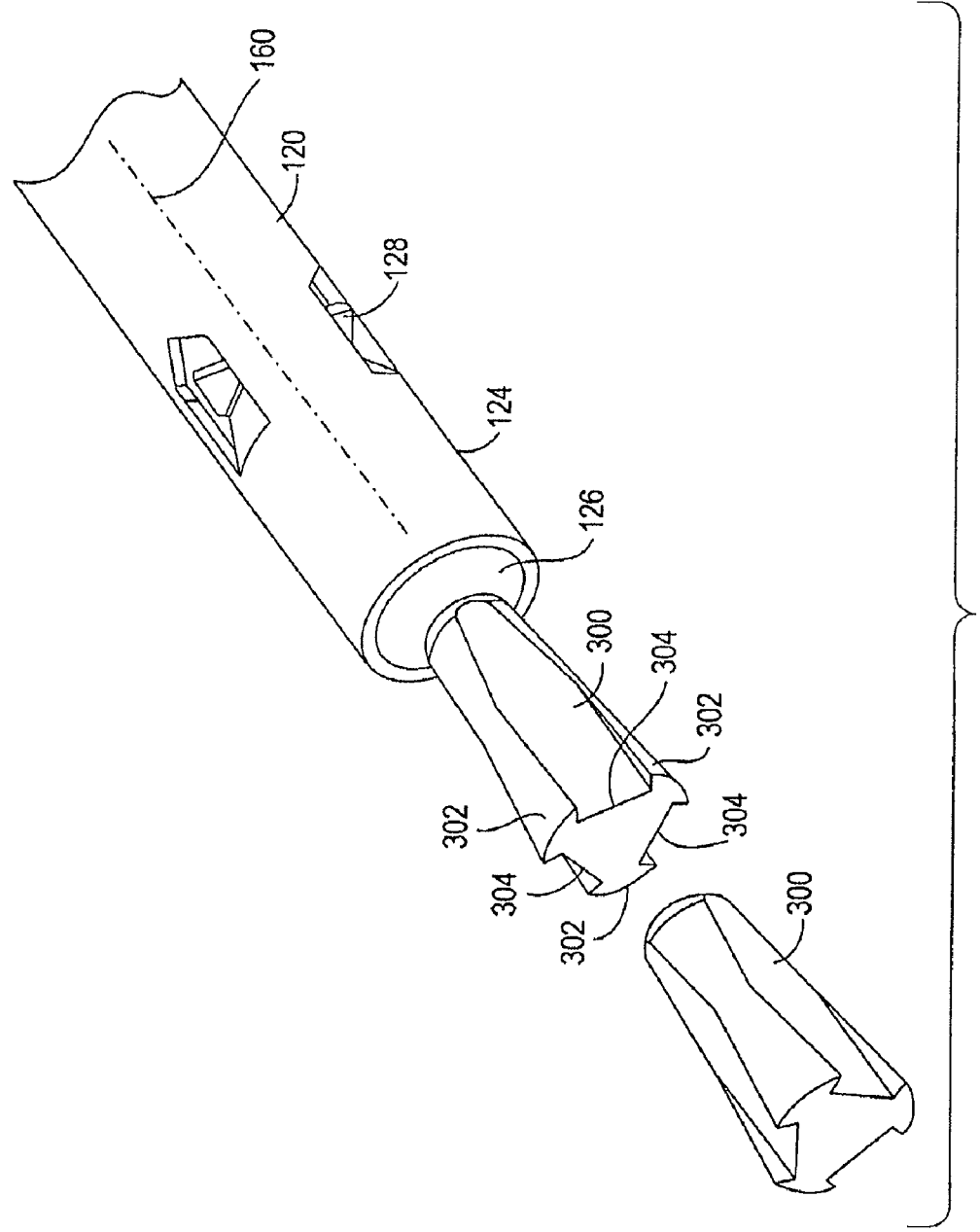
FIG. 4 is a perspective view of a bone treatment kit constructed in accordance with still another embodiment of the invention, particularly showing an alternative actuator that can be used with the intramedullary bone shaft of FIG. 1.

In the previous embodiments, the actuators 130, 230 take the form of a single elongated member that is capable of deploying all of the anchoring elements 128. Alternatively, a series of actuators can be used to deploy the anchoring elements 128. For example, FIG. 4 illustrates two actuators 300 that can be used with the bone shaft 120. In the illustrated embodiment, each actuator 300 takes the form of pellet that is sized to fit within the lumen 126 of the bone shaft 120. The actuator 300 has three longitudinally extending flat surfaces 302 and three longitudinally extending recesses 304 between the flat surfaces 302. Each of the three surfaces 302 are configured for engaging an anchoring element 128 of the bone shaft 120.

An advantage of using an actuator that has one or more recesses 304 is that it allows a user to selectively deploy certain anchoring elements 128. Particularly, the actuator 300 can be oriented to align the recesses 304 with a set 150 of the anchoring elements 128 such that the actuator 300 can be advanced past the set 150 without deploying the anchoring elements 128.

Although two actuators 300 are shown, any suitable number of pellet-shaped actuators 300 can be used. In addition, in some embodiments, instead of using actuators that have the same configuration, actuators 300 having different configurations can be used. For example, actuators 300 having different cross-sectional dimensions, different number of surfaces 302 and/or recesses 304, or different lengths, can be provided, thereby allowing different anchoring elements 128 to be deployed in different manners along the length of the bone shaft 120. Furthermore, although the bone shaft 120 is shown, the actuators 300 can also be used with other bone shafts.

In one method of use, the surfaces 302 of the actuator 300 are aligned with circumferential positions of the anchoring elements 128 of the bone shaft 120, and the actuator 300 is then inserted into the lumen 126 at the second end 124. A plunger can be used to advance the actuator 300. As the actuator 300 is pushed distally towards the first end 122 of the bone shaft 120, the surfaces 302 of the actuator 300 engage any anchoring elements 128 that they come in contact with, and deploy the anchoring elements 128 at least partially out of the lumen 126. Additional actuator(s) 300 can also be inserted into the lumen, and be placed adjacent to the deployed anchoring elements 128, thereby preventing the deployed anchoring elements 128 from moving back towards their pre-deployed positions.

In one method, if the anchoring elements 128 at a first location along the axis 160 of the bone shaft 120 are circumferentially offset from the anchoring elements 128 at a second location along the axis of the bone shaft 120, the actuator 300 can be rotated at a desired orientation to engage the anchoring elements 128 while the actuator 300 is within the lumen 126. For example, referring to FIG. 1, after a first set 150a of the anchoring elements 128 have been deployed by the actuator 300, the actuator 300 can be further advanced to deploy a second set 150b of the anchoring elements 128. In such cases, the plunger that is used to advance the actuator 300 is detachably attached to the actuator 300, and can be used to rotate the actuator 300.

Particularly, after the actuator 300 has deployed the first set 150a of the anchoring elements 128, but before the actuator 300 reaches the second set 150b, the plunger can be rotated to change an orientation of the actuator 300 such that the surfaces 302 align with the second sets 150b of the anchoring elements 128. The actuator 300 is then advanced distally towards the first end 122 to deploy the second set 150b of the anchoring elements 128 by manipulating the plunger. In some cases, if a certain set 150 of the anchoring elements 128 is not desired to be deployed, the plunger can be manipulated to rotate the actuator 300 such that the recesses 304 are aligned with the respective anchoring elements 128. The plunger is then advanced distally to push the actuator 300 pass the set 150 of the anchoring elements 128 without deploying the anchoring elements 128. As the plunger is advanced distally, it can be rotated to orient the actuator 300 such that the actuator 300 can deploy or avoid the anchoring elements 128 along the bone shaft 120, until the actuator 300 reaches the first end 122 or a desired position. The anchor 300 is then released from the plunger. Various methods known in the art can be used to detachably attach the actuator 300 to the plunger. For examples, the actuator 300 can be attached to the plunger via an mechanical connection that is operable to release the actuator 300, or via an electrolytic connection that can be dissolved to release the actuator 300.

Figure 5:
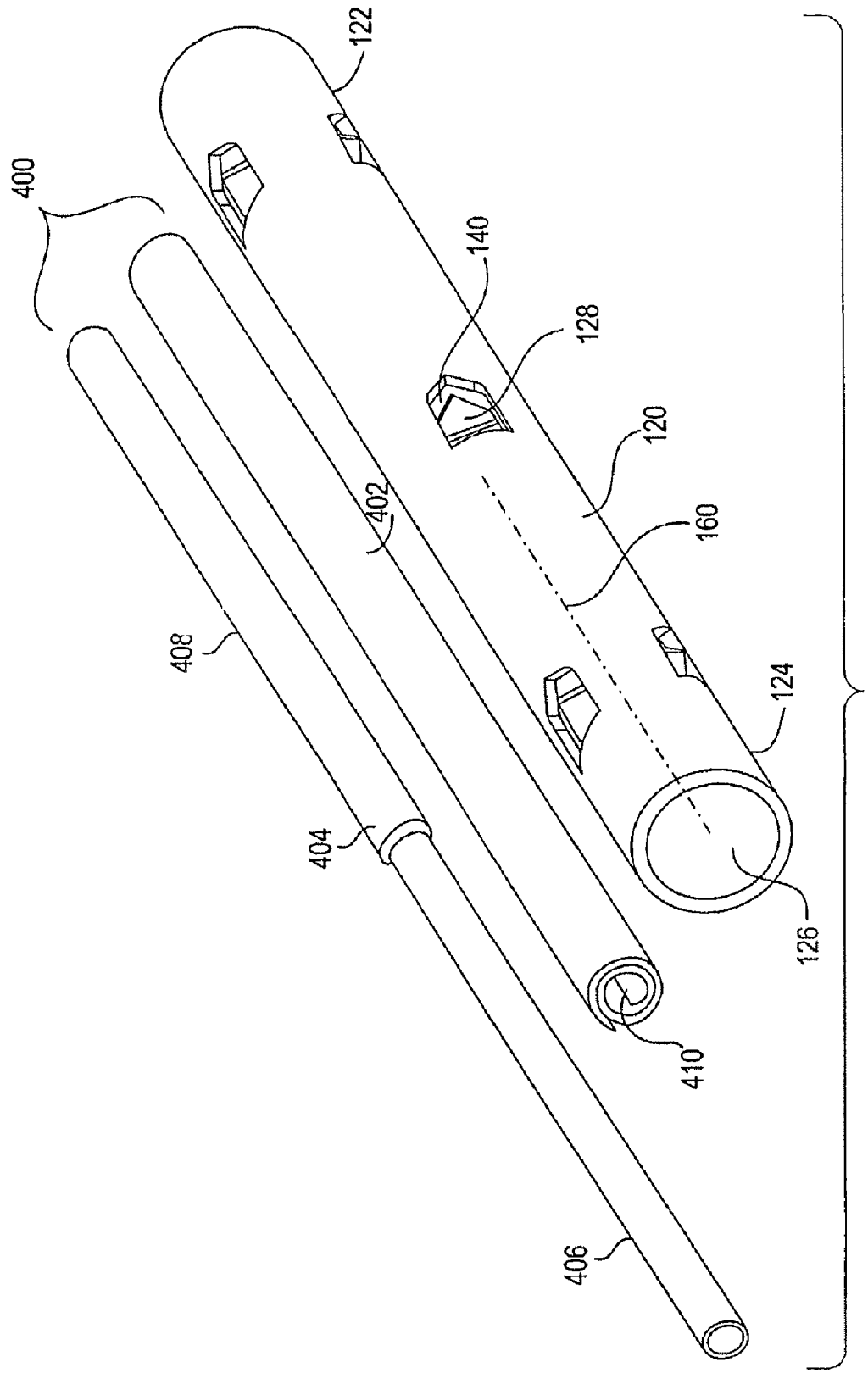
FIG. 5 is a perspective view of a bone treatment kit constructed in accordance with yet another embodiment of the invention, particularly showing another alternative actuator that can be used with the intramedullary bone shaft of FIG. 1.

FIG. 5 illustrates another embodiment of an actuator 400 that can be used with the bone shaft 120 or other tubular structures described herein. The actuator 400 includes an expandable rolled-up tube 402 and an expander 404. The expandable tube 402, which has a spiral cross-sectional shape, is capable of changing its cross-sectional dimension in response to an object placed inside its central lumen 410. The expander 404 has a first elongated member 406, and a second elongated member 408 coaxially surrounding the first member 406 in a telescoping fashion. The members 406, 408 each has a cross-sectional dimension that is larger than a cross-sectional dimension of the lumen 410 when the tube 402 is in its relaxed configuration (i.e., unstretched state).

During use, the tube 402 is initially inserted into the lumen 126 of the bone shaft 120 (FIG. 6A). The first member 406 of the expander 404 is then inserted into the lumen 410 of the tube 402. Because the first member 406 has a cross-sectional dimension that is larger than that of the lumen 410, the first member 406 exerts a pressure from within the lumen 410, and pushes open (or "un-rolls") the rolled-up tube 402, thereby increasing the overall cross-sectional dimension of the tube 402. The expanded tube 402, in turn, engages the anchoring elements 128 and deploys the anchoring elements 128 at least partially out of the lumen 126 (FIG. 6B). If desired, the second member 408 can be inserted between the tube 402 and the first member 406 to further expand the tube 402, and further deploy the anchoring elements 128 (FIG. 6C). Although two members 406, 408 are shown, in alternative embodiments, the expander 404 can include only one member, or other number of members that are coaxially disposed relative to each other. The actuator 400 and the expander 404 can be made from any of the materials described previously with reference to the bone shaft 120.

In alternative embodiments, instead of using the rolled-up tube 402, any of the intramedullary devices described herein can include other expandable structures, such as an inflatable member, an expandable mesh, or other mechanical devices, which can be inserted into the lumen 126 of the bone shaft 120 and be expanded to deploy the anchoring elements 128.

Figure 7:
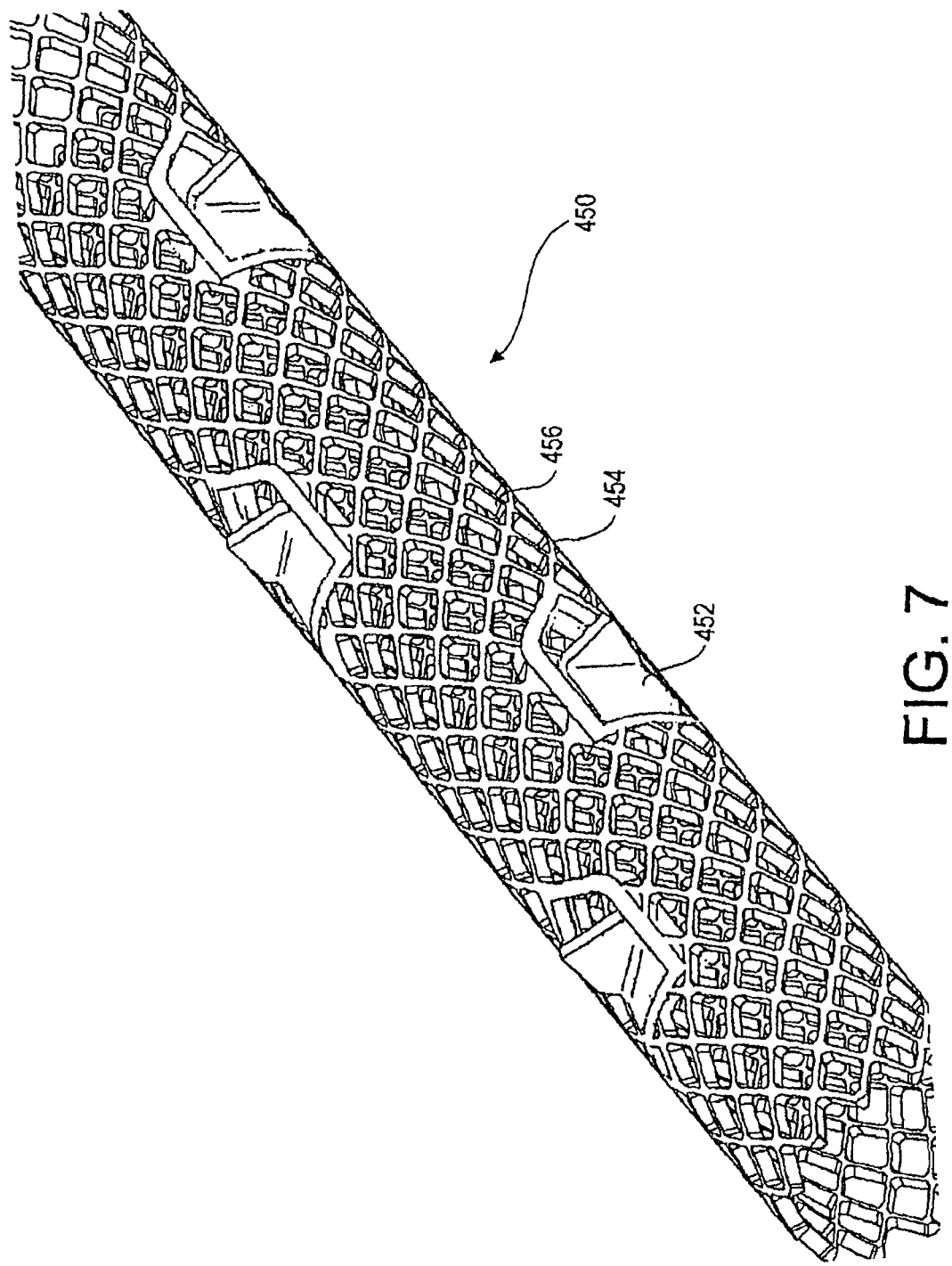
FIG. 7 is a partially cutaway perspective view of an alternative intramedullary bone shaft that can be used in any of the previous bone treatment kits.

In the previously described embodiments, the bones shafts 120, 220 have a substantially continuous and smooth surface between the anchoring elements. However, any of the bone shafts described herein can be porous in nature. For example, FIG. 7 shows a bone treatment shaft 450 having a wall 454 that includes a plurality of openings (or pores) 456 between anchoring elements 452. Such configuration is desirable because it allows surrounding bone tissue to grow through the openings 456 at the wall 454 of the tubular shaft 450, thereby improving anchoring of the bone shaft 450 to the surround bone tissue. Although the openings 456 have a square shape, alternatively, the openings 456 can have other shapes, such as a circular shape, an elliptical shape, a triangular shape, a rectangular shape, a slotted shape, or other customized shapes, and may also have open sections in part or along the wall.

Although the previous devices have been described as single elongated bone shafts that extend only along the medullary canal of a bone, it should be appreciated that other types of devices incorporating the anchoring concepts disclosed herein can be employed.

Figure 8:
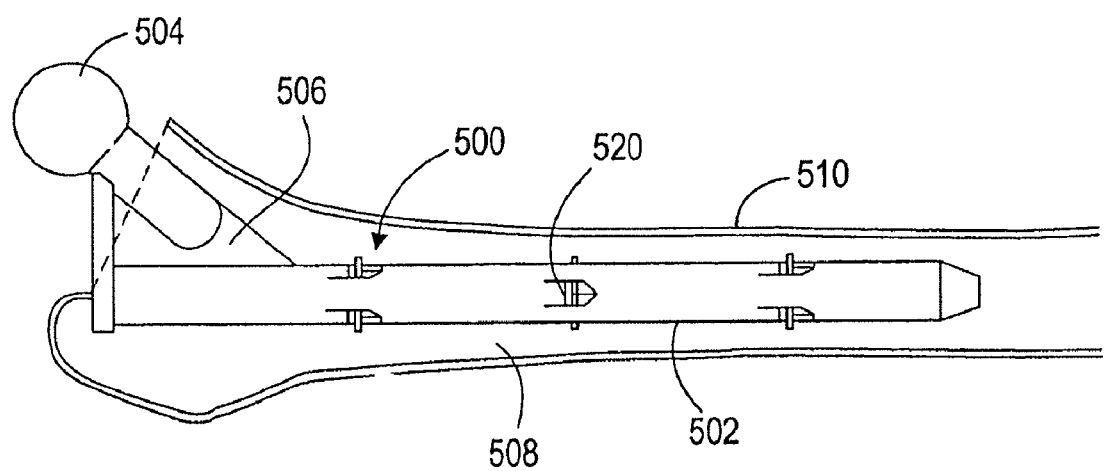
FIG. 8 is a side view of one embodiment of a bone treatment device that incorporates features of any of the previously described bone treatment kits to anchor itself within the medullary canal of a bone.

For example, FIG. 8 illustrates an intramedullary device 500 having a bone shaft 502, a ball joint 504, and a connecting member 506 securing the ball joint 504 to the bone shaft 502 (forming a hip joint replacement segment). In the illustrated embodiments, the intramedullary device 500 is configured to be inserted into a medullary cavity 508 of a femur 510. In other embodiments, the intramedullary device 500 can be configured to treat other joints and bones. When the device 500 is desirably placed, the ball joint 504 should be located in the area where the head of the femur was previously located. The shaft 502, which includes a plurality of anchoring elements 520, is similar to the bone shaft 120 discussed previously. After the device 500 is desirably placed, any of the actuators described previously can be inserted into the shaft 502 to deploy the anchoring elements 520, thereby securing the shaft 502 relative to the femur 510. In the illustrated embodiments, the ball joint 504 and the connecting member 506 are manufactured with the shaft 502 as one unit. Alternatively, the ball joint 504 and the connecting member 506 can be manufactured separately from the shaft 502. In such cases, ball joints 504 having different sizes and shapes can be made, and a desired ball joint can be selected to couple with the shaft 502 to suit a particular application (modular). In other embodiments, the connecting member 506 can be made shorter. Also, in further embodiments, the connecting member 506 is not needed, in which case, the ball joint 504 can be connected directly to the shaft 502, or indirectly to the shaft 502 by another connecting structure.

Figure 9A:
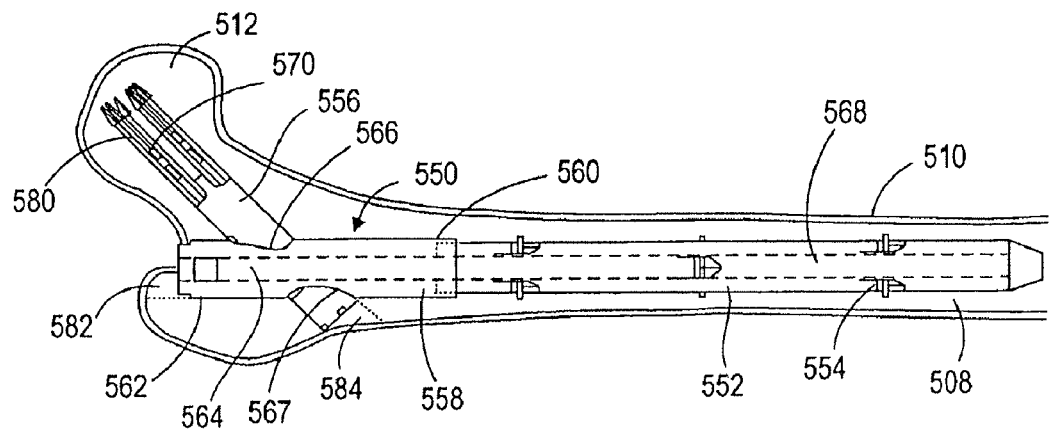
FIGS. 9A and 9B are side views of another embodiment of a bone treatment device that incorporates features of any of the previously described bone treatment kits to anchor itself within the medullary canal of a bone.
Figure 9B:
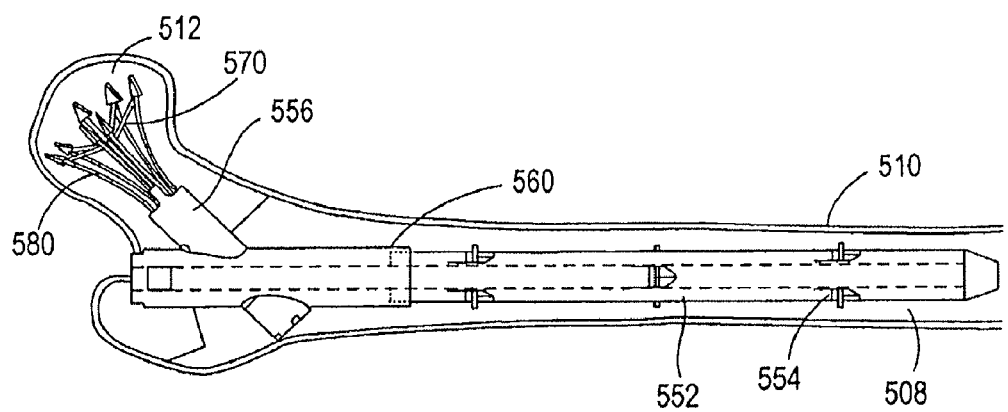

FIG. 9A illustrates another intramedullary device 550 having a first bone shaft 552, a second bone shaft 556, and a connecting member 558 connecting the shafts 552, 556. The first bone shaft 552 is similar to the bone shaft 120 discussed previously. The connecting member 558 has a first end 560, a second end 562, and a lumen 564 extending between the first and the second ends 560, 562. The first bone shaft 552 is secured to the first end 560 of the connecting member 558 such that the lumen 564 of the connecting member 558 is aligned with a lumen 568 of the first bone shaft 552. Alternatively, the first bone shaft 552 and the connecting member 558 can be manufactured as a single unit. The connecting member 558 also has a first opening 566 on one side of a wall, and a second opening 567 on an opposite side of a wall. The openings 566, 567 are aligned such that the second bone shaft 556 can extend through both openings 566, 567 at any desired angle relative to the bone shaft 552. The second bone shaft 556 includes a plurality of splines 570, and support arms 580 for expanding the splines 570 from a generally axial collapsed state to a substantially transverse expanded state (FIG. 9B). Bone devices having splines and support arms have been described in U.S. patent application Ser. No. 10/349,210, the entire disclosure of which is expressly incorporated by reference herein. In other embodiments, the second shaft 556 can have anchoring elements that are similar to those of the first shaft 552. The anchoring elements can be at an end or along part(s) of the second shaft 556. In further embodiments, the second shaft 556 can be a screw, or a set of screws, a rod, or a wire a bone device of another shapes.

When using the device 550, the first bone shaft 552 and the connecting member 558 are first inserted through a previously formed entry portal 582 into the medullary canal 508 of the femur 510 using conventional methods. Any of the actuators described herein can then be inserted into the lumen 568 of the first bone shaft 552 to deploy the anchoring elements 554, thereby securing the first bone shaft 552 relative to the femur 510. Next, the second bone shaft 556 is inserted through another entry portal 584, and through the openings 566, 567 of the connecting member 558, such that the splines 570 is positioned within the epiphyseal area 512. Another actuator can then be inserted into a lumen of the second bone shaft 556 to engage the support arms 580. The actuator is then advanced distally to deploy the splines 570, thereby securing the second bone shaft 556 relative to the femur 510. In some embodiments, the device 550 can be used to treat fractures of the neck of femur, intertrochanteric and subtrochanteric area of the femur.

Figure 10:
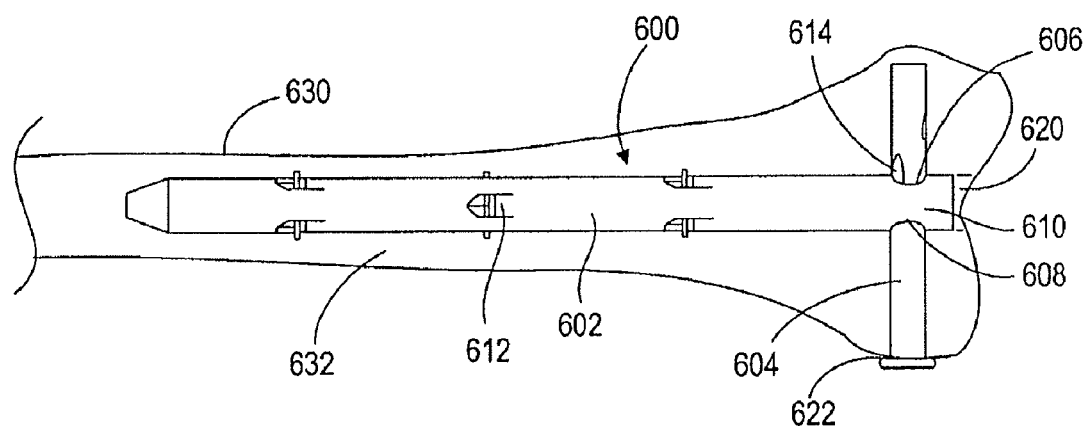
FIG. 10 is a side view of still another embodiment of a bone treatment device that incorporates features of any of the previously described bone treatment kits to anchor itself within the medullary canal of a bone.

FIG. 10 illustrates another intramedullary device 600 having a first bone shaft 602 and a second bone shaft 604. The bone shafts 602, 604 include a plurality of respective anchoring elements 612, 614, and are similar to the bone shaft 120 discussed previous, except that the first bone shaft 602 further includes a first opening 606 and a second opening 608 at one end 610. The first and the second openings 606, 608 are aligned such that the second bone shaft 604 can extend through both openings 606, 608.

When using the device 600, the first bone shaft 602 is first inserted through a previously formed entry portal 620 into a medullary canal 632 of the femur 630 using conventional methods. Any of the actuators described herein can then be inserted into a lumen of the first bone shaft 602 to deploy the anchoring elements 612, thereby securing the first bone shaft 602 relative to the femur 630. Next, the second bone shaft 604 is inserted through another entry portal 622, and through the first and the second openings 606, 608 of the first bone shaft 602. Another actuator can then be inserted into a lumen of the second bone shaft 604 to deploy the anchoring elements 614.

In the illustrated embodiments, the implanted positions of the bone shafts 602, 604 are such that they are approximately 90° from each other. Alternatively, the bone shafts 602, 604 can form other angles relative to each other, depending on the particular application. In other embodiments, instead of using the bone shaft 604, a bone screw can be used. As shown in the illustrated embodiments, the device 600 is used to treat fractures of the distal end of the femur. However, in other embodiments, the device 600 may be used to treat other bones, or for other applications.

It should be noted that the above described treatment devices are only examples in which embodiments of the invention can be implemented, and that any of the tubular shafts having anchoring elements described herein (or not described herein) can be a part of other treatment devices.

Figure 11:
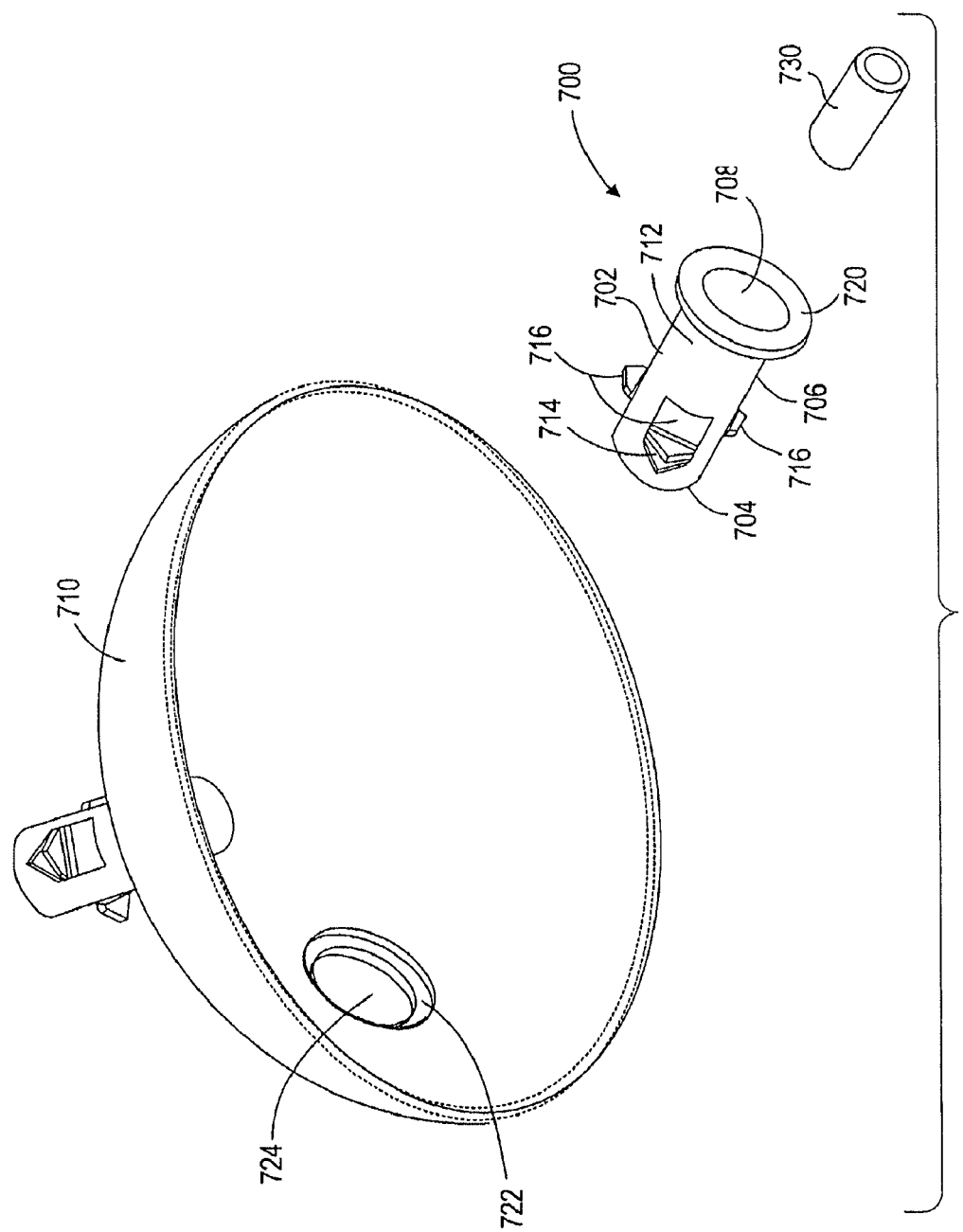
FIG. 11 is a side view of yet another embodiment of a bone treatment device that incorporates features of any of the previously described bone treatment kits to laterally anchor itself onto the side of a bone.

FIG. 11 illustrates a bone treatment kit 700 that can be used to secure a structure 710 to a bone. The structure 710 can be a socket of a joint replacement part for a hip or a shoulder, or a base that holds a joint surface in a knee replacement prosthesis, for examples. The kit 700 includes a bone shaft 702 having a first end 704, a second end 706, and a wall 712 defining a lumen 708 that extends from the first end 704 to the second end 706.

The bone shaft 702 also includes a plurality of openings 714 and respective plurality of anchoring elements 716 located adjacent the openings 714. The bone shaft 702 is similar to the bone shaft 120 except that the shaft 702 is relatively shorter. The bone shaft 702 also includes an annular flange 720 secured to the second end 706. The annular flange 720 is sized to fit within a recess 722 of the structure 710 or to bear against a surface of the structure 710 during use. When using the device 700 to secure the structure 710 to a bone, the bone is first prepared in the former joint surface to create a bone bed for the replacement part. The structure 710 is then placed against the bone, and the device 700 is inserted into an opening 724 at the structure 710 after drilling holes in the bone to create a fitting place for device 700. The first end 704 of the bone shaft 702 is advanced through the opening 724 and into the drilled hole. The bone shaft 702 is further distally advanced until the annular flange 720 bears against a surface of the structure 710. Next, a pellet-shaped actuator 730 is inserted into the lumen 708 of the bone shaft 702 to deploy the anchoring elements 716, thereby securing the shaft 702 relative to the bone. As such, the bone shaft 702 functions as a nail that secures the structure 710 to the bone.

It should be noted that in alternative embodiments, instead of the flange 720, the bone shaft 702 can include a washer, threads on an exterior surface of the shaft 702 (for receiving a bolt), threads in an interior surface of the shaft 702 (for receiving a screw), a hole through the wall of the shaft 702 for receiving a pin, or other mechanisms for allowing the shaft 702 to secure the structure 710 in place. Also, in other embodiments, a portion of the shaft 702 can be made wider (e.g., by bending an end portion of the shaft 702 radially away from an axis of the shaft 702), thereby allowing the shaft 702 to be used to hold the structure 710 in place.

Figure 12:
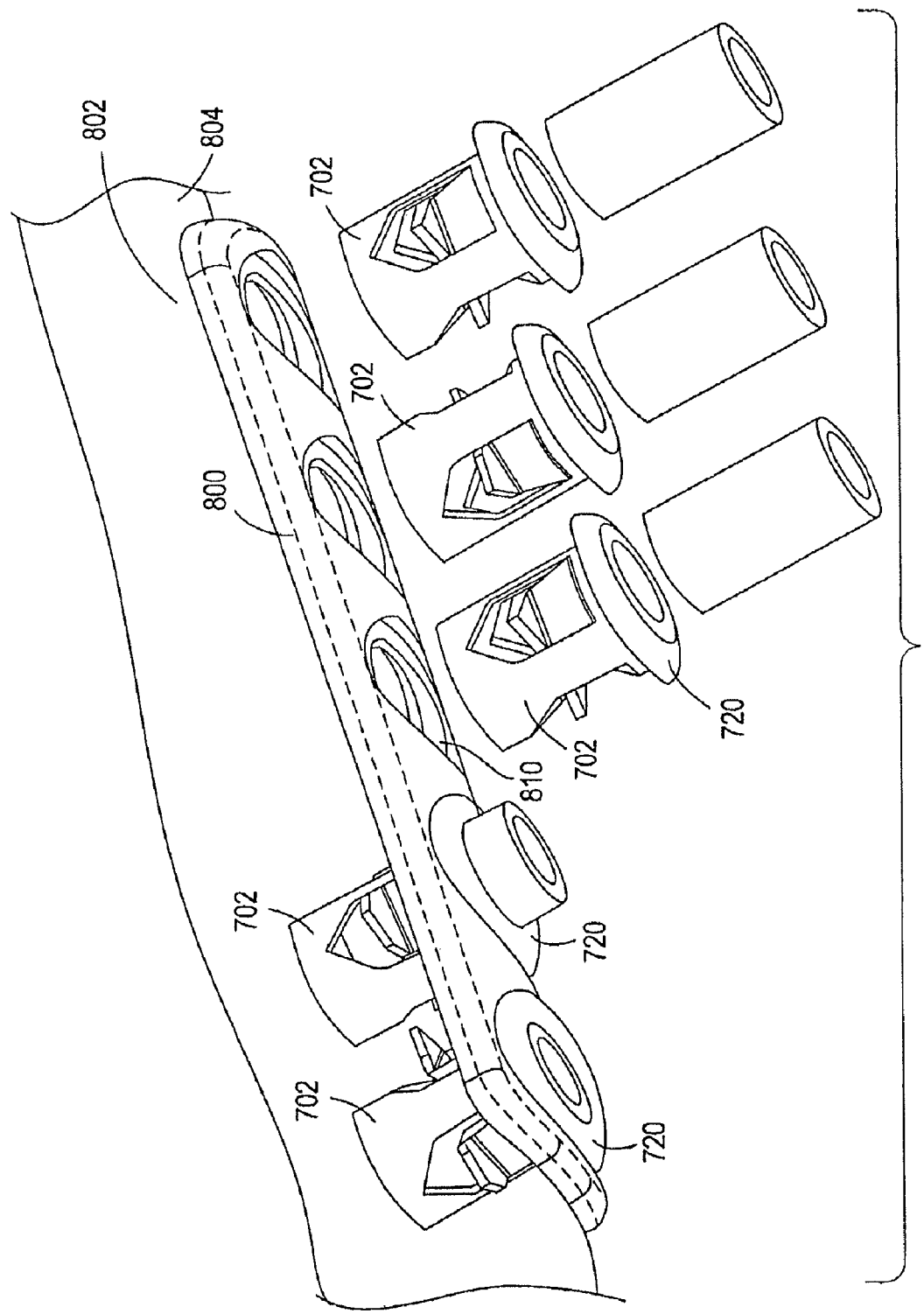
FIG. 12 is side view of yet another embodiment of a bone treatment device that incorporates features of any of the previously described bone treatment kits to anchor itself to the side of a bone.

FIG. 12 illustrates that a plurality of bone shafts 702 can be used to secure a plate 800 to an exterior surface 802 of a bone 804. The plate 800 includes a plurality of recesses 810 sized to accommodate the annular flanges 720 of the bone shafts 702. In alternative embodiments, the bone shafts 702 can also be used to secure other structures, such as a post, a partial joint replacement device, or a total joint replacement device, to a bone. In other embodiments, the bone shafts 702 can also be used to secure other structures, such as a tendon, a ligament, or an artificial ligament, to a bone. In other embodiments, the bone shaft 702 can be configured to be inserted through one cortex of a bone (in which case, the shaft 702 can be made relatively short in length), or both cortices of the bone (in which case, the shaft 702 can be made relatively longer), with anchoring elements after the first cortex, the second cortex, or both.

Although particular embodiments of the invention have been shown and described, the specification and drawings are to be regarded in an illustrative rather than restrictive sense, and it will be apparent to those skilled in the art that various changes and modifications may be made without departing from the scope of the invention, as defined in the following claims.

What is claimed is.

1. A bone treatment device comprising:
   a biocompatible shaft having a tubular wall, said tubular wall defining a shaft lumen and at least one opening through the tubular wall, the at least one opening being in communication with the shaft lumen;
   at least one bone anchoring element coupled to the tubular wall adjacent the at least one opening, the at least one bone anchoring element being configured and dimensioned to be moveable between at least: (i) a first position inside the shaft lumen in the absence of an engaging actuating force within the shaft lumen; and (ii) a second position at least partially out of the at least one opening in the presence of an engaging actuating force within the shaft lumen; and
   an actuator configured to be received within the shaft lumen to provide the engaging actuating force to deploy the at least one anchoring element from the first position inside the shaft lumen to the second position at least partially out of the at least one opening;
   wherein the presence of the engaging actuating force within the shaft lumen prevents the at least one engaged bone anchoring element from moving to the first position inside the shaft lumen; and
   wherein the actuator is axially and substantially non-rotationally moved within the shaft lumen to deploy the at least one anchoring element from the first position inside the shaft lumen to the second position at least partially out of the at least one opening;
   wherein the actuator is configured to be placed within a first rotational orietation that does not deploy the at least one anchoring element when the actuator is axially moved by the at least one anchoring element, and a second rotational orientation that deploys the at least one anchoring element when the actuator is axially moved by the at least one anchoring element.

2. The device of claim 1, wherein the tubular wall has a substantially continuous surface.

3. The device of claim 1, wherein the tubular wall is composed of a mesh.

4. The device of claim 1, wherein the tubular wall is rigid.

5. The device of claim 1, wherein the at least one anchoring element and tubular wall are formed as a unibody structure.

6. The device of claim 1, wherein the at least one opening comprises a plurality of openings axially disposed along the tubular wall, and wherein the at least one anchoring element comprises a plurality of anchoring elements coupled to the tubular wall adjacent the respective openings.

7. The device of claim 1, wherein the at least one anchoring element has an outwardly extending tip.

8. The device of claim 1, wherein the shapes of the at least one anchoring element and the at least one opening are geometrically similar.

9. The device of claim 1, wherein the at least one opening is located at an end of the tubular wall.

10. The device of claim 1, wherein the shaft is inserted into a fractured bone, and the deployment of the at least one anchoring element to the second position stabilizes the fractured bone.

11. The device of claim 1, wherein the shaft is inserted into a bone to couple an object to the bone, the object selected from the group consisting of a joint prosthetic section, a tendon, a ligament, a plate, a flange, an adaptor, a connector, a rod, an interconnecting element, a hook, a transducer, a tooth or a bridge on the jaws, a tissue engineered material, a matrix, a scaffold, a bone graft, an allograft tissue, and a muscle.

12. The device of claim 1, wherein the at least one anchoring element is hingedly coupled to the tubular wall, and the actuator is configured to deploy the at least one hingedly coupled anchoring element from the first position inside the shaft lumen to the second position at least partially out of the at least one opening.

13. The device of claim 1, wherein the actuator is removable from the shaft lumen after the actuator has deployed the at least one anchoring element from the first position to the second position.

14. A bone treatment device comprising:
   a biocompatible shaft having a tubular wall, wherein the tubular wall is rigid, said tubular wall defining a shaft lumen and at least one opening through the tubular wall, the at least one opening being in communication with the shaft lumen;
   at least one bone anchoring element coupled to the tubular wall adjacent the at least one opening, the at least one bone anchoring element being configured and dimensioned to be plastically deformable between at least: (i) a first position inside the shaft lumen in the absence of an engaging actuating force within the shaft lumen; and (ii)

a second position at least partially out of the at least one opening in the presence of an engaging actuating force within the shaft lumen; and an actuator configured to be received within the shaft lumen to provide the engaging actuating force to plastically deform the at least one anchoring element from the first position inside the shaft lumen to the second position at least partially out of the at least one opening;

wherein the presence of the engaging actuating force within the shaft lumen prevents the at least one engaged bone anchoring element from being plastically deformed to the first position inside the shaft lumen;

wherein the actuator comprises a first member disposed within the shaft lumen, and a second member disposed within a lumen of the first member, the second member being non-threadably coupled to the first member, and wherein the actuator is axially and substantially non-rotationally moved within the shaft lumen to plastically deform the at least one anchoring element from the first position to the second position.

15. The device of claim 14, wherein the tubular wall has a substantially continuous surface.

16. The device of claim 14, wherein the tubular wall is composed of a mesh.

17. The device of claim 14, wherein the at least one anchoring element and tubular wall are formed as a unibody structure.

18. The device of claim 14, wherein the at least one opening comprises a plurality of openings axially disposed along the tubular wall, and wherein the at least one anchoring element comprises a plurality of anchoring elements coupled to the tubular wall adjacent the respective openings.

19. The device of claim 14, wherein the at least one anchoring element has an outwardly extending tip.

20. The device of claim 14, wherein the shapes of the at least one anchoring element and the at least one opening are geometrically similar.

21. The device of claim 14, wherein the at least one opening is located at an end of the tubular wall.

22. The device of claim 14, wherein the shaft is inserted into a fractured bone, and the plastic deformation of the at least one anchoring element to the second position stabilizes the fractured bone.

23. The device of claim 14, wherein the shaft is inserted into a bone to couple an object to the bone, the object selected from the group consisting of a joint prosthetic section, a tendon, a ligament, a plate, a flange, an adaptor, a connector, a rod, an interconnecting element, a hook, a transducer, a tooth or a bridge on the jaws, a tissue engineered material, a matrix, a scaffold, a bone graft, an allograft tissue, and a muscle.

24. The device of claim 14, wherein the at least one anchoring element is hingedly coupled to the tubular wall, and the actuator is configured to plastically deform the at least one hingedly coupled anchoring element from the first position inside the shaft lumen to the second position at least partially out of the at least one opening.

25. The device of claim 14, wherein the actuator is configured to be placed within a first rotational orientation that does not plastically deform the at least one anchoring element when the actuator is axially moved by the at least one anchoring element, and a second rotational orientation that plastically deforms the at least one anchoring element when the actuator is axially moved by the at least one anchoring element.

26. The device of claim 14, wherein the actuator is removable from the shaft lumen after the actuator has deployed the at least one anchoring element from the first position to the second position.

* * * * *